(12) United States Patent
Eskuri

(10) Patent No.: US 9,326,774 B2
(45) Date of Patent: May 3, 2016

(54) DEVICE FOR IMPLANTATION OF MEDICAL DEVICES

(75) Inventor: Alan Eskuri, Irvine, CA (US)

(73) Assignee: Covidien LP, Mansfield, MA (US)

( * ) Notice: Subject to any disclaimer, the term of this patent is extended or adjusted under 35 U.S.C. 154(b) by 545 days.

(21) Appl. No.: 13/565,859

(22) Filed: Aug. 3, 2012

(65) Prior Publication Data

US 2014/0039535 A1   Feb. 6, 2014

(51) Int. Cl.
*A61F 2/06* (2013.01)
*A61B 17/12* (2006.01)

(52) U.S. Cl.
CPC ... *A61B 17/12022* (2013.01); *A61B 2017/1209* (2013.01); *A61B 2017/12063* (2013.01)

(58) Field of Classification Search
CPC .............. A61B 2017/12063; A61B 2017/1209
See application file for complete search history.

(56) References Cited

U.S. PATENT DOCUMENTS

| | | | |
|---|---|---|---|
| 5,108,407 A | 4/1992 | Geremia et al. |
| 5,122,136 A | 6/1992 | Guglielmi et al. |
| 5,250,071 A | 10/1993 | Palermo |
| 5,354,295 A | 10/1994 | Guglielmi et al. |
| 5,370,653 A | 12/1994 | Cragg |
| 5,423,829 A | 6/1995 | Pham et al. |
| 5,522,836 A | 6/1996 | Palermo |
| 5,540,680 A | 7/1996 | Guglielmi et al. |
| 5,624,449 A | 4/1997 | Pham et al. |
| 5,658,308 A | 8/1997 | Snyder |
| 5,690,667 A | 11/1997 | Gia |
| 5,733,329 A | 3/1998 | Wallace et al. |
| 5,743,905 A | 4/1998 | Eder et al. |
| 5,749,894 A | 5/1998 | Engelson |
| 5,766,629 A | 6/1998 | Cho et al. |
| 5,800,455 A | 9/1998 | Palermo et al. |
| 5,851,206 A | 12/1998 | Guglielmi et al. |
| 5,853,418 A | 12/1998 | Ken et al. |
| 5,855,578 A | 1/1999 | Guglielmi et al. |
| 5,891,128 A | 4/1999 | Gia et al. |
| 5,895,385 A | 4/1999 | Guglielmi et al. |
| 5,916,235 A | 6/1999 | Guglielmi |
| 5,919,187 A | 7/1999 | Guglielmi et al. |
| 5,925,037 A | 7/1999 | Guglielmi et al. |
| 5,925,059 A | 7/1999 | Palermo et al. |

(Continued)

FOREIGN PATENT DOCUMENTS

| | | |
|---|---|---|
| DE | 4445715 | 6/1996 |
| DE | 10118017 | 10/2002 |

(Continued)

OTHER PUBLICATIONS

U.S. Appl. No. 13/916,770, filed Jun. 13, 2013.

*Primary Examiner* — Robert Lynch
(74) *Attorney, Agent, or Firm* — Mark J. Kertz, Esq.

(57) ABSTRACT

An apparatus for implanting a medical device is provided that can be severed by electrolysis from a delivery member positioned in a patient. The apparatus can include an electrolytically detachable component that interconnects the medical device and the delivery member. The detachable component can have at least one corrodible first portion being adapted to serve as an anode in electrolytic corrosion. The at least one first portion can define a body having an outer surface and at least one surface structure extending inwardly from the outer surface into the body. The first portion can be electrolytically corrodible when in contact with a body fluid such that the medical device may be severed by electrolysis.

24 Claims, 5 Drawing Sheets

(56) References Cited

U.S. PATENT DOCUMENTS

| | | |
|---|---|---|
| 5,928,226 A | 7/1999 | Guglielmi et al. |
| 5,935,145 A | 8/1999 | Villar et al. |
| 5,941,888 A | 8/1999 | Wallace et al. |
| 5,944,714 A | 8/1999 | Guglielmi et al. |
| 5,947,962 A | 9/1999 | Guglielmi et al. |
| 5,947,963 A | 9/1999 | Guglielmi |
| 5,964,797 A | 10/1999 | Ho |
| 5,976,126 A | 11/1999 | Guglielmi |
| 5,984,929 A | 11/1999 | Bashiri et al. |
| 6,010,498 A | 1/2000 | Guglielmi |
| 6,013,084 A | 1/2000 | Ken et al. |
| 6,059,779 A | 5/2000 | Mills |
| 6,063,070 A | 5/2000 | Eder |
| 6,063,104 A | 5/2000 | Villar et al. |
| 6,066,133 A | 5/2000 | Guglielmi et al. |
| 6,077,260 A | 6/2000 | Wheelock et al. |
| 6,083,220 A | 7/2000 | Guglielmi et al. |
| 6,123,714 A | 9/2000 | Gia et al. |
| 6,136,015 A | 10/2000 | Kurz et al. |
| 6,146,373 A | 11/2000 | Cragg et al. |
| 6,156,061 A | 12/2000 | Wallace et al. |
| 6,165,178 A | 12/2000 | Bashiri et al. |
| 6,168,592 B1 | 1/2001 | Kupiecki et al. |
| 6,168,615 B1 | 1/2001 | Ken et al. |
| 6,168,618 B1 | 1/2001 | Frantzen |
| 6,193,728 B1 | 2/2001 | Ken et al. |
| 6,238,403 B1 | 5/2001 | Greene, Jr. et al. |
| 6,241,691 B1 | 6/2001 | Ferrera et al. |
| 6,280,457 B1 | 8/2001 | Wallace et al. |
| 6,296,622 B1 | 10/2001 | Kurz et al. |
| 6,299,619 B1 | 10/2001 | Greene, Jr. et al. |
| 6,306,153 B1 | 10/2001 | Kurz et al. |
| 6,371,972 B1 | 4/2002 | Wallace et al. |
| 6,409,721 B1 | 6/2002 | Wheelock et al. |
| 6,416,373 B1 | 7/2002 | Kolb et al. |
| 6,425,893 B1 | 7/2002 | Guglielmi |
| 6,425,914 B1 | 7/2002 | Wallace et al. |
| 6,468,266 B1 | 10/2002 | Bashiri et al. |
| 6,468,301 B1 | 10/2002 | Amplatz et al. |
| 6,478,773 B1 | 11/2002 | Gandhi et al. |
| 6,485,524 B2 | 11/2002 | Strecker |
| 6,486,266 B2 | 11/2002 | Amano et al. |
| 6,511,468 B1 | 1/2003 | Cragg et al. |
| 6,533,801 B2 | 3/2003 | Wallace et al. |
| 6,558,367 B1 | 5/2003 | Cragg et al. |
| 6,589,230 B2 | 7/2003 | Gia et al. |
| 6,589,236 B2 | 7/2003 | Wheelock et al. |
| 6,602,261 B2 | 8/2003 | Greene, Jr. et al. |
| 6,620,152 B2 | 9/2003 | Guglielmi |
| 6,623,493 B2 | 9/2003 | Wallace et al. |
| 6,723,112 B2 | 4/2004 | Ho et al. |
| 6,743,251 B1 | 6/2004 | Eder |
| 6,835,185 B2 | 12/2004 | Ramzipoor et al. |
| 6,905,503 B2 | 6/2005 | Gifford, III et al. |
| 6,936,055 B1 | 8/2005 | Ken et al. |
| 6,953,473 B2 | 10/2005 | Porter |
| 6,964,657 B2 | 11/2005 | Cragg et al. |
| 6,966,892 B2 | 11/2005 | Gandhi et al. |
| 7,014,645 B2 | 3/2006 | Greene, Jr. et al. |
| 7,083,567 B2 | 8/2006 | Mawad |
| 7,128,736 B1 | 10/2006 | Abrams et al. |
| 7,166,122 B2 | 1/2007 | Aganon et al. |
| 7,169,172 B2 | 1/2007 | Levine et al. |
| 7,198,613 B2 | 4/2007 | Gandhi et al. |
| 7,238,194 B2 | 7/2007 | Monstadt et al. |
| 7,255,707 B2 | 8/2007 | Ramzipoor et al. |
| 7,300,458 B2 | 11/2007 | Henkes et al. |
| 7,323,000 B2 | 1/2008 | Monstdt et al. |
| 7,331,974 B2 | 2/2008 | Schaefer et al. |
| 7,485,122 B2 | 2/2009 | Teoh |
| 7,524,322 B2 | 4/2009 | Monstdt et al. |
| 7,608,089 B2 | 10/2009 | Wallace et al. |
| RE41,029 E | 12/2009 | Guglielmi et al. |
| 7,651,513 B2 | 1/2010 | Teoh et al. |
| 7,695,484 B2 | 4/2010 | Wallace et al. |
| 7,879,064 B2 | 2/2011 | Monstadt et al. |
| 7,896,899 B2 | 3/2011 | Patterson et al. |
| 7,938,845 B2 | 5/2011 | Aganon et al. |
| 8,002,789 B2 | 8/2011 | Ramzipoor et al. |
| RE42,756 E | 9/2011 | Guglielmi et al. |
| 8,016,869 B2 | 9/2011 | Nikolchev |
| 8,021,416 B2 | 9/2011 | Abrams |
| 8,048,104 B2 | 11/2011 | Monstadt et al. |
| RE43,311 E | 4/2012 | Wallace et al. |
| 8,157,855 B2 | 4/2012 | Eidenschink et al. |
| 8,202,292 B2 | 6/2012 | Kellett |
| 8,221,396 B2 | 7/2012 | Dehnad et al. |
| 8,221,483 B2 | 7/2012 | Ford et al. |
| 8,273,116 B2 | 9/2012 | Licata et al. |
| 8,298,256 B2 | 10/2012 | Gandhi et al. |
| 8,328,860 B2 | 12/2012 | Strauss et al. |
| 8,372,110 B2 | 2/2013 | Monstadt et al. |
| 8,398,671 B2 | 3/2013 | Chen et al. |
| 8,480,701 B2 | 7/2013 | Monstadt |
| 8,562,667 B2 | 10/2013 | Cox |
| 8,597,321 B2 | 12/2013 | Monstadt et al. |
| 8,632,584 B2 | 1/2014 | Henkes et al. |
| 8,641,746 B2 | 2/2014 | Andreas et al. |
| 8,641,777 B2 | 2/2014 | Strauss et al. |
| 8,652,163 B2 | 2/2014 | Padilla et al. |
| 8,657,870 B2 | 2/2014 | Turovskiy et al. |
| 8,715,312 B2 | 5/2014 | Burke et al. |
| 8,721,625 B2 | 5/2014 | Klint |
| 8,728,142 B2 | 5/2014 | Gandhi et al. |
| 8,777,978 B2 | 7/2014 | Strauss et al. |
| 8,777,979 B2 | 7/2014 | Shrivastava et al. |
| 8,795,320 B2 | 8/2014 | Strauss et al. |
| 8,795,321 B2 | 8/2014 | Strauss et al. |
| 8,801,747 B2 | 8/2014 | Strauss et al. |
| 8,845,676 B2 | 9/2014 | Monstadt et al. |
| 8,864,790 B2 | 10/2014 | Strauss et al. |
| 8,870,909 B2 | 10/2014 | Cox |
| 8,876,863 B2 | 11/2014 | Eskridge |
| 8,900,285 B2 | 12/2014 | Licata |
| 8,915,950 B2 | 12/2014 | Cam et al. |
| 8,926,681 B2 | 1/2015 | Levy et al. |
| 8,932,317 B2 | 1/2015 | Marks et al. |
| 8,940,011 B2 | 1/2015 | Teoh et al. |
| 8,974,509 B2 | 3/2015 | Licata |
| 8,974,513 B2 | 3/2015 | Ford et al. |
| 8,992,563 B2 | 3/2015 | Chen |
| 8,998,926 B2 | 4/2015 | Pomeranz |
| 9,039,749 B2 | 5/2015 | Shrivastava et al. |
| 9,050,095 B2 | 6/2015 | Monstadt et al. |
| 9,055,948 B2 | 6/2015 | Jaeger et al. |
| 2002/0151883 A1 | 10/2002 | Guglielmi |
| 2003/0014073 A1 | 1/2003 | Bashiri et al. |
| 2003/0040733 A1 | 2/2003 | Cragg et al. |
| 2003/0176857 A1 | 9/2003 | Lee |
| 2003/0225365 A1 | 12/2003 | Greff et al. |
| 2004/0002731 A1 | 1/2004 | Aganon et al. |
| 2004/0225279 A1 | 11/2004 | Raymond |
| 2005/0079196 A1 | 4/2005 | Henkes et al. |
| 2006/0036281 A1 | 2/2006 | Patterson et al. |
| 2006/0271097 A1* | 11/2006 | Ramzipoor et al. .......... 606/200 |
| 2007/0073334 A1* | 3/2007 | Ramzipoor .................. 606/200 |
| 2008/0045922 A1 | 2/2008 | Cragg et al. |
| 2008/0051803 A1 | 2/2008 | Monjtadt et al. |
| 2008/0103585 A1 | 5/2008 | Monstadt et al. |
| 2008/0125855 A1 | 5/2008 | Henkes et al. |
| 2008/0221666 A1 | 9/2008 | Licata et al. |
| 2008/0228215 A1 | 9/2008 | Strauss et al. |
| 2008/0228216 A1 | 9/2008 | Strauss et al. |
| 2008/0319532 A1 | 12/2008 | Monstadt et al. |
| 2009/0143786 A1 | 6/2009 | Bashiri et al. |
| 2009/0254111 A1 | 10/2009 | Monstadt et al. |
| 2010/0023105 A1 | 1/2010 | Levy et al. |
| 2010/0030200 A1 | 2/2010 | Strauss et al. |
| 2010/0049165 A1 | 2/2010 | Sutherland et al. |
| 2010/0063572 A1 | 3/2010 | Teoh et al. |
| 2010/0076479 A1 | 3/2010 | Monstadt |
| 2010/0331948 A1 | 12/2010 | Turovskiy et al. |
| 2011/0098814 A1 | 4/2011 | Monstadt et al. |
| 2011/0106128 A1 | 5/2011 | Chen |

(56) References Cited

U.S. PATENT DOCUMENTS

| | | | |
|---|---|---|---|
| 2011/0118777 | A1 | 5/2011 | Patterson et al. |
| 2011/0184453 | A1 | 7/2011 | Levy et al. |
| 2012/0010648 | A1 | 1/2012 | Monstadt et al. |
| 2012/0271344 | A1 | 10/2012 | Ford et al. |
| 2013/0138198 | A1 | 5/2013 | Aporta et al. |
| 2013/0184743 | A1 | 7/2013 | Chen et al. |
| 2013/0211492 | A1 | 8/2013 | Schneider et al. |
| 2014/0005651 | A1 | 1/2014 | Eskridge |
| 2014/0135818 | A1 | 5/2014 | Gandhi et al. |
| 2014/0142608 | A1 | 5/2014 | Eskridge et al. |
| 2014/0148843 | A1 | 5/2014 | Strauss et al. |
| 2014/0163604 | A1 | 6/2014 | Monstadt |
| 2014/0236217 | A1 | 8/2014 | Gandhi et al. |
| 2014/0277092 | A1 | 9/2014 | Teoh et al. |
| 2014/0277094 | A1 | 9/2014 | Chen et al. |
| 2014/0288633 | A1 | 9/2014 | Burke et al. |
| 2014/0371839 | A1 | 12/2014 | Henkes et al. |
| 2015/0005804 | A1 | 1/2015 | Franano et al. |
| 2015/0057700 | A1 | 2/2015 | Chen et al. |
| 2015/0066073 | A1 | 3/2015 | Ma |
| 2015/0105817 | A1 | 4/2015 | Marchand et al. |
| 2015/0133990 | A1 | 5/2015 | Davidson |
| 2015/0142042 | A1 | 5/2015 | Cox |
| 2015/0150563 | A1 | 6/2015 | Marchand et al. |
| 2015/0157331 | A1 | 6/2015 | Levy et al. |
| 2015/0164665 | A1 | 6/2015 | Cam et al. |
| 2015/0173771 | A1 | 6/2015 | Marks et al. |

FOREIGN PATENT DOCUMENTS

| | | | |
|---|---|---|---|
| EP | 484468 | | 5/1992 |
| EP | 719522 | | 7/1996 |
| EP | 726745 | | 8/1996 |
| EP | 803230 | A2 | 10/1997 |
| EP | 807410 | A2 | 11/1997 |
| EP | 861634 | A2 | 9/1998 |
| EP | 1005837 | A2 | 6/2000 |
| EP | 1009295 | | 6/2000 |
| EP | 1227760 | | 8/2002 |
| EP | 1329196 | | 7/2003 |
| EP | 1420701 | A1 | 5/2004 |
| EP | 1843710 | A1 | 10/2007 |
| EP | 1884208 | A1 | 2/2008 |
| EP | 1951129 | A2 | 8/2008 |
| EP | 2124763 | A2 | 12/2009 |
| EP | 2146651 | A2 | 1/2010 |
| EP | 2227163 | A1 | 9/2010 |
| EP | 2334242 | A1 | 6/2011 |
| EP | 2415424 | A2 | 2/2012 |
| EP | 2575697 | A1 | 4/2013 |
| EP | 2668914 | A1 | 12/2013 |
| EP | 2781196 | A2 | 9/2014 |
| EP | 2859854 | A1 | 4/2015 |
| WO | WO-91/13592 | | 9/1991 |
| WO | WO-95/12367 | | 5/1995 |
| WO | WO-99/09894 | | 3/1999 |
| WO | WO 01/32085 | | 5/2001 |

\* cited by examiner

DEVICE FOR IMPLANTATION OF MEDICAL DEVICES

BACKGROUND

The use of endovascular techniques for the implantation of medical devices and the occlusion of body cavities such as arteries, veins, fallopian tubes or vascular deformities is known in the art. For example, occlusion of vascular aneurysms can be performed using an implantable device, such as an occlusion spiral, that is introduced with the aid of an endovascular guide wire through a catheter. Once moved to the treatment site, the occlusion spiral can be moved into the aneurysm cavity to occlude the aneurysm.

The severance of the occluding spiral from the endovascular guide wire can be particular technically problematic. On the one hand, the device must be as small as possible to be guided through the fine bore of the catheter to its destination, while on the other hand it must bring about a reliable severance of the occluding spiral. Absent a reliable severance of the occluding spiral, withdrawal of the guide wire and catheter may cause unintended removal of the occluding spiral from the cavity to be occluded and thus injure and/or rupture of the wall of the cavity or vessel.

Mechanical methods for the severance of occluding spirals from the insertion means do not take much time to perform. However, the necessary rigidity of the technical features of the connection between the occluding spiral and the introduction means impede the introduction of the implant. Furthermore, the low load carrying capacity of the connection due to its rigidity entails a not inappreciable risk of premature detachment of the insertion means from the occluding implant. Moreover, in the case of mechanical separation of the inserting wire and the occluding spiral, energy must be transmitted (as a rule by rotation of the inserting wire), and this may mean that the implant is dislodged out of the correct position.

Electrolytic severance of the occluding spiral involves using an electrolytically corrodible design on the end of the guide wire at the connection between the guide wire and the occluding spiral. Such a device can elegantly makes use of the voltage applied to the occluding spiral serving as an anode for electro-thrombization. However, for the simultaneous severance of the wire end and the occluding spiral thereon, such a device suffers, just like the above-mentioned mechanical severance method, from the disadvantage that only implants of predetermined length can be detached or severed. It has therefore been considered generally necessary that the doctor determine the length or longitudinal extent of the occluding spiral directly prior to the insertion of the implant, on the basis of the size of the cavity to be occluded. Since the irregular form of body cavities to be occluded makes it difficult to correctly assess the length of the occluding spiral necessary for filling, there is the likelihood of excessively long or excessively short occluding spirals being introduced into the cavity to be occluded, something which may involve on the one hand an incomplete occlusion or on the other hand injury to or rupture of the wall of the cavity (or of contiguous vessels) to be occluded.

A further disadvantage of the electrolytic severance of the end of the guide wire is that for production of the guide wire, the only materials that can be utilized are those which have a sufficiently high degree of strength to enable reliable guidance of the occluding wire through the guide wire. The selection of materials for forming the point of eventual electrolytic severance is consequently extremely limited.

In the case of prior art devices for the electrolytic severance of occluding spirals, the occluding spiral and the guide wire are not produced integrally, but instead are produced mechanically connected with each other. This design has the inherent disadvantage that the guide wire must be tapered toward its end in an involved grinding operation in order to ensure sufficient strength in the proximal zone of the guide wire and to facilitate electrolytic, corrosive severance of the wire end in the distal part of the guide wire. In order to ensure sufficient strength of the connection point, the corrodible zone of the end of the guide wire must not have a diameter below a certain minimum value since it is subjected to a high flexural load. The corrodible wire end representing the connection point between the occluding spiral and the guide wire can be consequently extremely rigid and require a relatively long time for electrolytic corrosive severance.

SUMMARY

Electrolytic severance of the implantable medical devices can involve using an electrolytically corrodible design on the end of the guide wire at the connection between the guide wire and the medical device. Such a device can elegantly makes use of the voltage applied to the occluding spiral serving as an anode for electro-thrombization. However, for the simultaneous severance of the wire end and the medical device thereon, such a device suffers, just like the above-mentioned mechanical severance method, from the disadvantage that only implants of predetermined length can be detached or severed. It has therefore been considered generally advisable that the doctor determine the length or longitudinal extent of the occluding spiral directly prior to the insertion of the implant, on the basis of the size of the cavity to be occluded. Since the irregular form of body cavities to be occluded makes it difficult to correctly assess the length of the occluding spiral necessary for filling, there is the likelihood of excessively long or excessively short implantable devices being introduced into the cavity to be occluded, something which may involve on the one hand an incomplete occlusion or on the other hand injury to or rupture of the wall of the cavity (or of contiguous vessels) to be occluded.

A further disadvantage of the electrolytic severance of the end of the guide wire is that for production of the guide wire, the only materials that can be utilized are those which have a sufficiently high degree of strength to enable reliable guidance of the occluding wire through the guide wire. The selection of materials for forming the point of eventual electrolytic severance is consequently extremely limited.

In the case of electrolytic severance of occluding spirals, the occluding spiral and the guide wire are not produced integrally, but instead are produced mechanically connected with each other. This design has the inherent disadvantage that the guide wire must be tapered toward its end in an involved grinding operation in order to ensure sufficient strength in the proximal zone of the guide wire and to facilitate electrolytic, corrosive severance of the wire end in the distal part of the guide wire. In order to ensure sufficient strength of the connection point, the corrodible zone of the end of the guide wire must not have a diameter below a certain minimum value since it is subjected to a high flexural load. The corrodible wire end representing the connection point between the occluding spiral and the guide wire can be consequently extremely rigid and require a relatively long time for electrolytic corrosive severance.

At least one aspect of the disclosure provides methods and apparatuses for electrolytically detaching a device or devices (e.g., occluding devices, coils, or stents) that have been implanted into the body.

Some embodiments provide for a delivery system for implanting a medical device. The system can comprise a delivery member, a medical device, and an electorlytically detachable component. The delivery member can be configured for insertion into a patient. The medical device can be configured to be severed by electrolysis from the delivery member for placement in the patient. The electrolytically detachable component can interconnect the medical device and the delivery member. The detachable component can have at least one electrolytically corrodible first portion that is adapted to serve as an anode in electrolytic corrosion when in contact with a body fluid such that the medical device may be severed from the delivery member by electrolysis. The at least one first portion can define a body having an outer surface and at least one surface structure extending inwardly from the outer surface into the body such that the body has a cross-sectional profile that includes at least one peak and at least one valley.

In some embodiments, the at least one surface structure of the detachable component can be configured to provide an increased ratio of surface area to volume, compared to a detachable component that does not have such a structure. In particular, the presence of the structure can increase overall surface area of the component while decreasing the volume of the component. Accordingly, the ratio of the surface area to volume can increase, which can enhance the galvanic reaction. Various surface structures can be implemented to achieve an increase in the ratio of the surface area to volume. Such structures can include at least one trough, concavity, valley, recess, and/or indentation.

Further, in some embodiments, one or more other structures can be present on the detachable component to provide increased current density at such structure(s), compared to a detachable component that does not have such structure(s). With a higher current density at one or more areas of the component, the galvanic reaction can be faster, more predictable, and more effective for some embodiments. Such structures can include at least one bridge, edge, peak, trough, concavity, valley, recess, and/or indentation.

The at least one surface structure can extend in a longitudinal direction of the detachable component. The at least one surface structure can comprise a groove extending in a longitudinal direction of the detachable component. The first portion can define a cross-shaped cross section. The at least one surface structure can comprise a plurality of surface structures. Further, the plurality of surface structures can collectively form a rough surface on the first portion. The first portion can define a starburst shaped cross section. The first portion can also define a generally rectangular cross section having a perimeter formed with a plurality of peaks and valleys. The first portion can comprise an upper surface having a plurality of peaks and valleys fanned thereon. The first portion can also comprise a lower surface having a plurality of peaks and valleys formed thereon.

In some embodiments, the detachable component can be designed to be continuously electrically conductive in the proximal-to-distal direction. The detachable component can also comprise at least one non-corrodible second portion adjacent to the first portion.

Some embodiments can also comprise a source of electrical power, a cathode, and a catheter. In such embodiments, the detachable component, the medical device, and the delivery member can be configured to slide within the catheter.

In some embodiments, an electrolytically detachable component can be provided for interconnecting a medical device with a delivery member. The component can be adapted to serve as an anode to be severed by electrolysis in body cavities or blood vessels. The component can comprise a first portion attached to the medical device and the delivery member. The first portion can be electrolytically corrodible. The first portion can define a continuous, elongate body having at least one surface structure formed therein. The at least one surface structure can define a recess surface area on the first portion for enhancing electrolytic corrosion of the first portion when in contact with a body fluid.

The at least one surface structure can comprise an elongate trough extending in a longitudinal direction along the elongate body of the first portion. The elongate body of the first portion can defines a generally rectangular cross section. The elongate body of the first portion can define a cross-shaped cross section. The elongate body of the first portion can define a starburst shaped cross section. The elongate body of the first portion can define a cross section formed from at least one concavity and at least one convexity. Further, the at least one concavity can be formed by a pair of generally linear edges.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

In accordance with some embodiments disclosed herein is the realization that electrolytic detachment of a medical device from a delivery assembly can be improved by modifying the geometry of the corrodible connection between the medical device and the delivery assembly. Thus, various embodiments provide for unique corrodible connections that can facilitate electrolytic detachment of the medical device, making the detachment process faster and more reliable.

The medical device can be implanted in body cavities or blood vessels. In addition to the medical device, the delivery system can comprise a voltage source, a cathode, and a catheter. The medical device can be slid in the catheter in the longitudinal direction and adapted to serve as an anode, such that the medical device is designed to be electrolytically corroded at one or more points so that while in contact with a body fluid, one or more portions of the medical device may be severed by electrolysis.

In some embodiments, the delivery system and medical device can comprise a plurality of electrolytically corrodible points. Such embodiments can provide advantages over conventional systems. For example, when the medical device is an occluding spiral, the length, or quantity of the occluding spiral can be determined and not one, but various lengths of the same spiral may be severed in sequence and placed in the cavity to be occluded. This economizes not only as regards costs and time but also furthermore serves to further minimize surgery risks.

Figure 1:
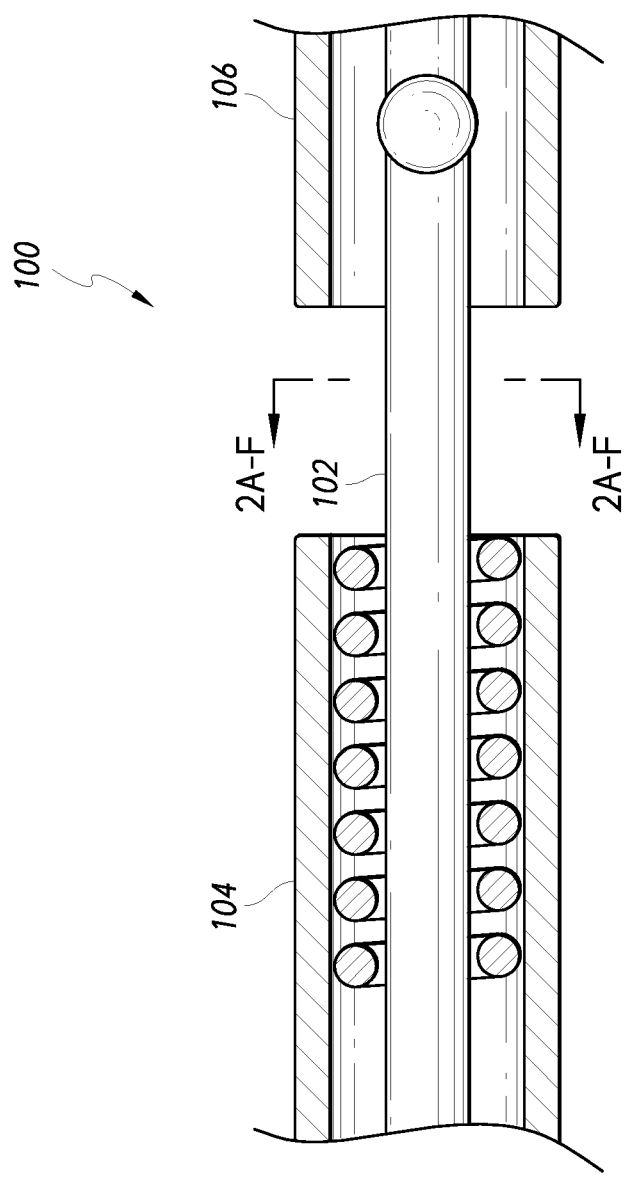
FIG. 1 is a partial cross-sectional view of a prior art delivery system.
Figure 2A:
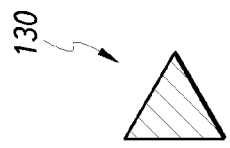
FIGS. 2A-F are cross-sectional views of possible connectors of the prior art delivery system shown in FIG. 1.
Figure 2B:
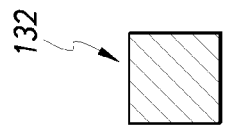
Figure 2C:
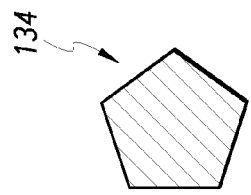
Figure 2D:
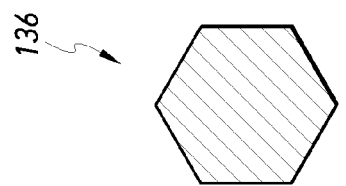
Figure 2E:
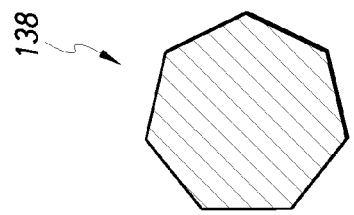
Figure 2F:
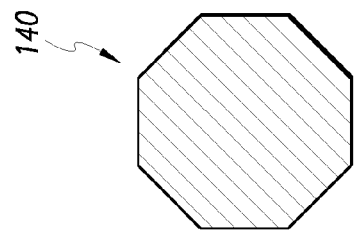

Embodiments disclosed herein contrast with prior art electrochemical connections, which do not provide the enhanced electrochemical corrosion rate in connection with durable or robust structural qualities. For example, FIG. 1 illustrates a cross section of a medical device delivery system 100 in which an electrolytically corrodible section 102 interconnects a medical device 104 and a delivery member 106. As known in the art, the delivery member 106 can comprise a voltage source, and the corrodible section 102 can act as an anode that degrades or corrodes upon the application of a voltage.

Figure 3:
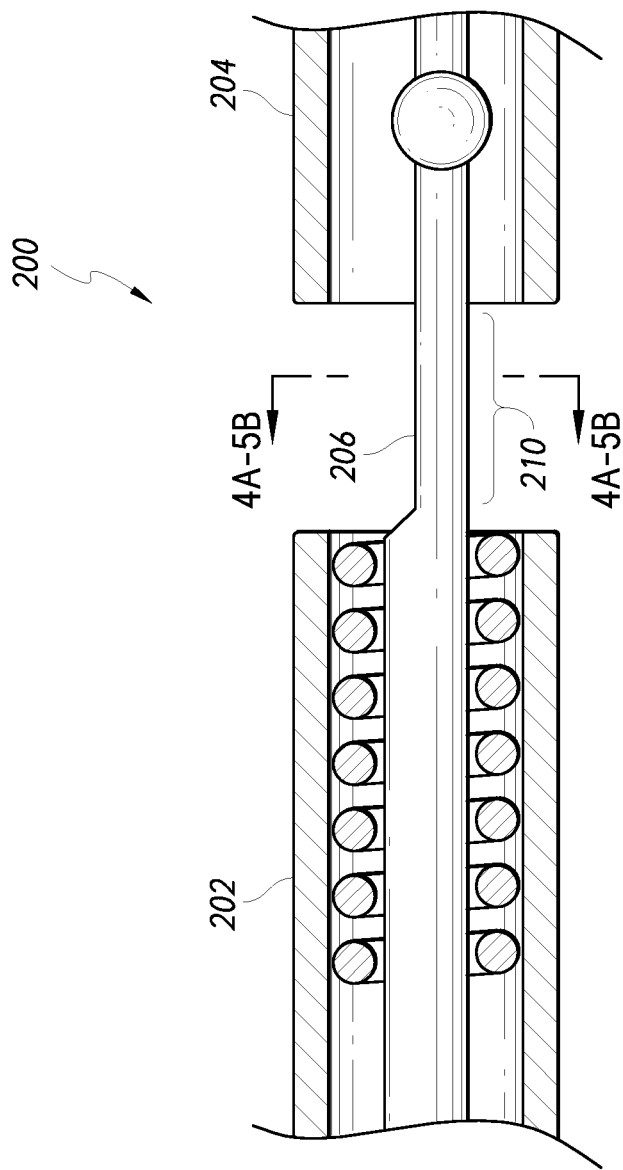
FIG. 3 is a partial cross-sectional view of a delivery system, in accordance with embodiments disclosed herein.

In contrast, embodiments disclosed herein provide unique improvements to not only the corrosion rate but also to the structural properties of corrodible sections. For example, referring to FIG. 3, an embodiment of a delivery system 200 is shown. The delivery system 200 can be configured to implant a medical device 202 that can be severed by electrolysis from a delivery member 204. The delivery system 200 can also comprise an electrolytically detachable section, or component 206 that interconnects the medical device 202 and the delivery member 204. The component 206 can have at least one corrodible portion or point 210 configured to serve as an anode during electrolytic corrosion.

The component 206 can be configured such that the corrodible portion or point 210 thereof defines a unique surface structure or texture configured to enhance electrolytic corrosion while preserving the structural characteristics of the component 206.

For example, the cross-sectional profile of the corrodible portion 210 of the component 206 can define at least one concavity, valley, recess, and/or indentation formed therein. In accordance with some embodiments, the cross-sectional profile of the corrodible portion 210 of the component 206 can define areas of positive curvature, such as one or more peaks, protrusions, and/or convexities, with areas of negative curvature, such as one or more valleys, recesses, concavities, and/or indentations. The one or more peaks, protrusions, and/or convexities and the one or more valleys, recesses, concavities, or indentations can be formed from surface structures such as grooves, channels, pits, threads, elongate troughs, circumferential or annular grooves, slots, apertures, coils, crimped ribbon, slotted ribbon, perforated ribbon, and/or other such structures that are precisely or randomly arranged. The shape of the cross-sectional profile of the connector body can be defined by one or more linear edges, parallel linear edges, intersecting linear edges, continuous curves, and/or combinations thereof.

For example, the cross-sectional profile of the component 206 can define at least one concavity, valley, recess, and/or indentation formed therein. In accordance with some embodiments, the cross-sectional profile of the component 206 can define areas of positive curvature, such as one or more peaks, protrusions, and/or convexities, with areas of negative curvature, such as one or more valleys, recesses, concavities, and/or indentations. The one or more peaks, protrusions, and/or convexities and the one or more valleys, recesses, concavities, or indentations can be formed from surface structures such as grooves, channels, pits, threads, elongate troughs, circumferential or annular grooves, slots, apertures, coils, crimped ribbon, slotted ribbon, perforated ribbon, and/or other such structures that are precisely or randomly arranged. The shape of the cross-sectional profile of the connector body can be defined by one or more linear edges, parallel linear edges, intersecting linear edges, continuous curves, and/or combinations thereof.

By providing a surface structure or texture, some embodiments can thereby provide an increased surface area of the component 206 in order to enhance the contact area of the component 206, reduce the overall volume of the component 206, and thereby improve the rate of corrosion. Further, various embodiments can be provided that are configured to provide excellent structural characteristics in order to ensure that the component 206 is sufficiently robust and durable.

For example, in some embodiments, the component can have a component body comprising at least one structure, such as a trough, valley, recess, concavity, or indentation defining a recess surface area. In accordance with some embodiments, the component can be configured such that the valley, recess, concavity, or indentation can be used in the component without reducing structural characteristics of the component.

Further, the structure of the component can add recess surface area to the overall surface area of the component, thereby enhancing electrolytic corrosion of the component. Thus, the component's ratio of surface area to volume can increase with an increase in overall surface area and a decrease in volume of the component. As discussed herein, the increase in the overall surface area of the component can be achieved by the incremental addition of surface area of the structure (e.g., the valley, recess, concavity, or indentation) versus the surface area of a surface without such a structure (e.g., a planar surface). The decrease in volume can be achieved by the addition of the void created by the valley, recess, concavity, or indentation.

Additionally, the detachable component can be fabricated to provide features that will lead to an increased current density in one or more areas of the component. Such features can include, for example, ridges, edges, small radius corners, valleys, troughs, concavities, recesses, indentations, and/or other structures. In some embodiments, the presence of some of these structures on the component can reduce the local cross sectional area and/or otherwise contribute to the galvanic reaction. Features that increase current density can accelerate the galvanic reaction.

Additionally, according to some embodiments, the electrolytically detachable component can be fabricated using a mechanical cold working operation. The cold working of the component can be performed through operations such as stamping, drawing, squeezing, bending, and/or other processes. The cold working of the component can enhance the galvanic reaction or corrosion. For example, as discussed herein, the component can comprise one or more structures or have a cross section that increases the surface area to volume ratio, which can enhance the galvanic reaction. Further, the process of cold working can alter the material properties of the component, which can improve the anodic quality or corrodibility of the component. Cold working can induce stresses in the material of the component, which can be released during the galvanic reaction, thus facilitating the galvanic reaction. Thus, fabrication of the component through a cold working operation can further enhance the galvanic reaction.

Figure 4A:
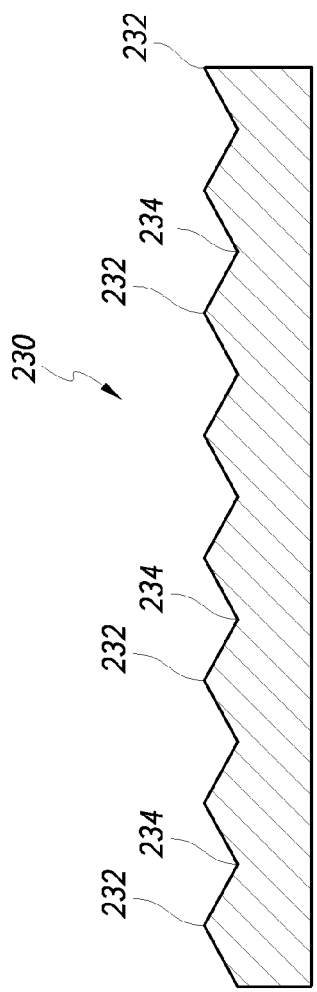
FIGS. 4A-B are cross-sectional views of possible connectors for use with the delivery system shown in FIG. 3, according to some embodiments.
Figure 4B:
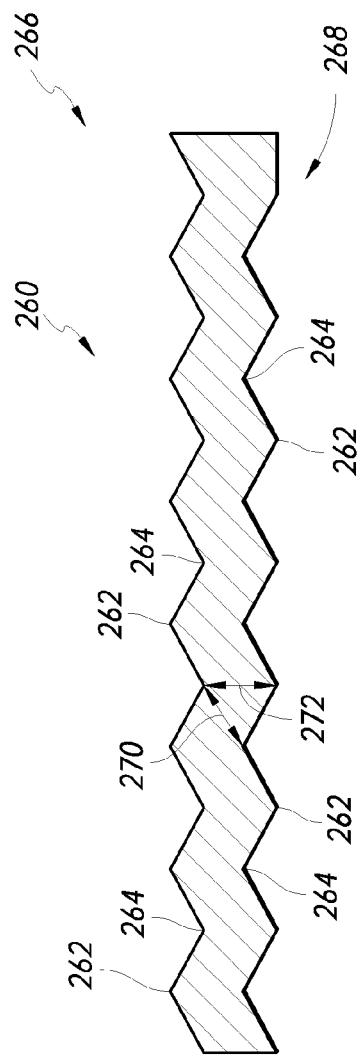

FIGS. 4A-B illustrate embodiments of a component which the component has a generally ribbon-shaped structure. Referring to FIG. 4A, a cross-sectional structure of a component body 230 can define a plurality of peaks, protrusions, or convexities 232 and valleys, recesses, or concavities 234. Such a configuration can be produced, for example, using a stamping manufacturing process. The plurality of valleys 234 can improve the rate of localized electrolytic degradation of the component body 230 in the areas immediately below the valleys 234, where the amount of material to be corroded is smallest. Further, the peaks 232 can provide a meaningful structural contribution to the overall strength of the component body 230, wherein the amount of material to be corroded is the greatest.

Similarly, FIG. 4B illustrates a cross-sectional structure of a component body 260 having a plurality of peaks, protrusions, or convexities 262 and valleys, recesses, or concavities 264. The component body 260 is configured such that the peaks, protrusions, or convexities 262 and valleys, recesses, or concavities 264 are formed along both upper and lower surfaces 266, 268 of the component body 260. The component body 260 can be characterized as a zigzag ribbon shape. In such an embodiment, a spacing 270 between adjacent valleys, recesses, or concavities 264 can be shorter than a spacing 272 between adjacent peaks, protrusions, or convexities 262. Thus, in some embodiments, adjacent valleys, recesses, or concavities can exhibit a faster rate of corrosion or degradation therebetween and thereby create corrosion bridges or holes that further increase the rate of corrosion of the component body.

In accordance with some embodiments, the structure (e.g., one or more peaks, protrusions, or convexities and one or more valleys, recesses, or concavities) can extend at least partially along the longitudinal length of the component body. For example, one or more peaks, protrusions, or convexities and/or one or more valleys, recesses, or concavities can extend along an entire length of the component body to provide a generally constant cross-sectional shape for the connector. However, the one or more peaks, protrusions, or convexities and/or the one or more valleys, recesses, or concavities can extend along between about one-third to about one-half of the entire length of the component body. Further, the one or more peaks, protrusions, or convexities and/or the one or more valleys, recesses, or concavities can extend along about less than one-third of the entire length of the component body. Furthermore, in accordance with some embodiments, the one or more peaks, protrusions, or convexities and/or the one or more valleys, recesses, or concavities can comprise discrete indentations or pits that collectively form a surface roughness along at least a portion of the length of the component body.

Additionally, in some embodiments, the component body can comprise first and second sets of structures. For example, a first set of structures (e.g., peaks, protrusions, or convexities and/or valleys, recesses, or concavities) having a first amplitude or size can be provided on the component body, and a second set of structures (e.g., peaks, protrusions, or convexities and/or valleys, recesses, or concavities) having a second amplitude or size can be provided on the first set of structures. The first and second amplitudes can be different. Thus, the sizes of the first and second sets of structures can be configured such that the amplitude of the first set of structures is about 50% to about 500% as great as the amplitude of the second set of structures.

Furthermore, in accordance with some embodiments, the component body can comprise a hollow portion that extends at least partially along the length of the component body. The hollow portion can be formed as a discrete bubble or as an internal tubular vacuity extending within the component body. In accordance with some embodiments, the tubular vacuity can extend longitudinally within the component body. The hollow portion can define one or more sections that are exposed or open to an exterior of the connector body. Accordingly, in such embodiments, the rate of corrosion can be enhanced. Further, it is possible to thereby provide one or more areas where corrosion can be accelerated significantly as the corrosion process reaches the hollow portion(s) of the component body. As such, one or more hollow portions can be present at one or more sections or points along the component body.

Figure 5B:
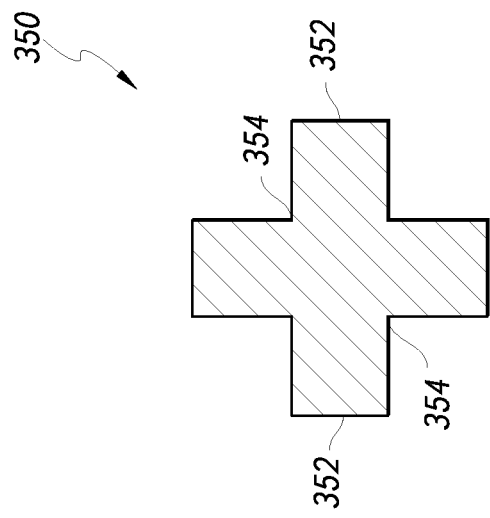
FIGS. 5A-B are cross-sectional views of other possible connectors for use with the delivery system shown in FIG. 3, according to some embodiments.
Figure 5A:
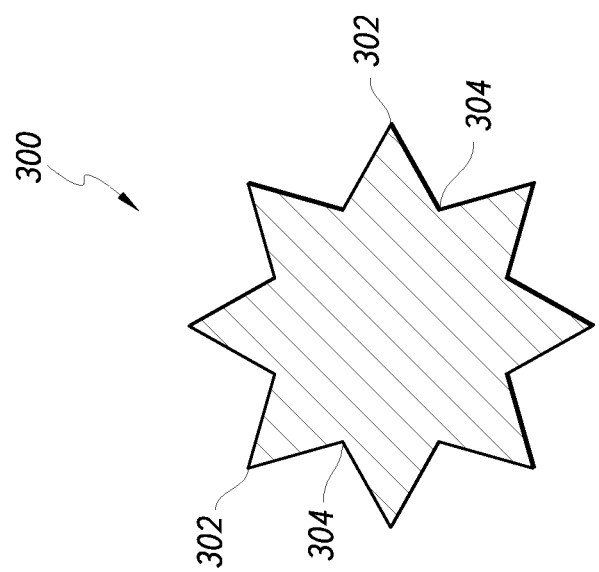

Referring now to FIGS. 5A-B, alternative embodiments of a cross-sectional profile of a connector body are shown. FIG. 5A illustrates a connector body 300 having a structure with a starburst-shaped cross-sectional profile in which the connector body 300 comprises a plurality of protrusions 302 and recesses 304. Similarly, FIG. 5B illustrates a connector body 350 having a structure with a cross-shaped cross-sectional profile in which the connector body 350 comprises a plurality of protrusions 352 and recesses 354. The structures of these cross-sectional profiles can provide portions of reduced volume and/or negative curvature that can accelerate electrolytic degradation of the connector body. As will be appreciated, various other cross-sectional profiles can be provided which can include structures such as recesses or perimeter cutouts that reduce the volume of the connector body and which can avoid negatively affecting the structural characteristics of the connector body.

Accordingly, in some embodiments, as well as those illustrated in FIGS. 4A-5B, the presence of the surface structure(s) on the detachable component can provide an increased ratio of surface area to volume, compared to a detachable component that does not have such a structure. Thus, with a higher ratio of surface area to volume, the galvanic reaction can be faster, more predictable, and more effective for some embodiments.

Further, in some embodiments, as well as those illustrated in FIGS. 4A-5B, the presence of a surface feature(s) on the detachable component can provide increased current density at such feature(s), compared to a detachable component that does not have such a feature(s). With a higher current density, the galvanic reaction can be faster, more predictable, and more effective for some embodiments.

Other features and discussion of electrolytically corrodible connections is provided in other applications of the present assignee, including the discussion and disclosure of U.S. Patent Application Publication No. 2012/0010648 and U.S. Pat. Nos. 7,323,000, and 8,048,104, the entirety of each of which is incorporated herein by reference.

The electrolytically non-corrodible sections of the medical device can contain one or more of the following materials: noble metals or noble metal alloys, corrosion-resistant ceramic materials, corrosion-resistant plastics, and preferably platinum metal alloys.

The electrolytically corrodible point can comprise one or more of the following materials: ceramic materials, plastics, base metals or alloys thereof, and preferably stainless steel. Some of the most suitable material combinations for forming the electrolytically corrodible points can include one or more of the following: stainless steels, preferably of the type AISI 301, 304, 316, or subgroups thereof; Ti or TiNi alloys; Co-based alloys; noble metals; or noble metal alloys, such as Pt, Pt metals, Pt alloys, Au alloys, or Sn alloys. Further, ceramic materials and plastics employed for forming the medical device can be electrically conductive.

The use of the above mentioned materials for the formation of the electrolytically non-corrodible sections and of the electrolytically corrodible points of the medical device ensure specific electrolytic corrosion of the medical device at the predetermined points.

One or more electrolytically corrodible points on the medical device can be constituted by fittings, which can be placed between electrolytically non-corrodible fractions of the medical device. Such embodiments possess the advantage that a particularly large number of different materials may be combined with one another for the formation of the electrolytically corrodible points and the electrolytically non-corrodible sections. Such embodiments can also be advantageous in that the electrolytically corrodible points and the electrolytically non-corrodible sections may be modularly joined together to form medical devices of a variable or desired length. Fittings that serve as electrolytically corrodible points can be connected with the non-corrodible sections by soldering, brazing, bonding, welding, or by mechanical joining operations, such as clamping or crimping.

In accordance with some embodiments, the electrolytically corrodible points can also be pre-corroded by etching or other methods. Thus, the structure(s) of a given cross-sectional profile can be modified to reduce the presence of corners, increase the recess depth, and/or otherwise enhance the corrosion rate. Further, various excellent structural designs can be provided to achieve desired corrosion performance through the teachings disclosed herein without pre-corrosion of the corrodible points.

Some embodiments can include corrodible points that have a partial coating of a material to provide a greater or lesser electrochemical resistance. Thus, in embodiments that have one or more corrodible points, the electrochemical resistance of the points can be varied to achieve staged or preferential electrochemical resistance. Coatings of Zn, Sn, or alloys of such metals on fittings of stainless steel have been found to be particularly satisfactory. Further, some embodiments, the end of the guide wire can be insulated, for example, by a material coating with reduced corrosion properties or a shrunk-on sleeve to improve its electrochemical resistance.

Embodiments disclosed herein can be used in veterinary or human medicine and more particularly, for the endovascular treatment of intracranial aneurysms and acquired or innate arteriovenous blood vessel deformities and/or fistulas and/or for the embolization of tumors by thrombozation.

The apparatus and methods discussed herein are not limited to the deployment and use of an occluding device within any particular vessels, but can include any number of different types of vessels. For example, in some aspects, vessels can include arteries or veins. In some aspects, the vessels can be suprathoracic vessels (e.g., vessels in the neck or above), intrathoracic vessels (e.g., vessels in the thorax), subthoracic vessels (e.g., vessels in the abdominal area or below), lateral thoracic vessels (e.g., vessels to the sides of the thorax such as vessels in the shoulder area and beyond), or other types of vessels and/or branches thereof.

In some aspects, the stent delivery systems disclosed herein can be deployed within superthoraeic vessels. The suprathoracic vessels can comprise at least one of intracranial vessels, cerebral arteries, and/or any branches thereof. For example, the suprathoracic vessels can comprise at least one of a common carotid artery, an internal carotid artery, an external carotid artery, a middle meningeal artery, superficial temporal arteries, an occipital artery, a lacrimal (ophthalmic) artery, an accessory meningeal artery, an anterior ethmoidal artery, a posterior ethmoidal artery, a maxillary artery, a posterior auricular artery, an ascending pharyngeal artery, a vertebral artery, a left middle meningeal artery, a posterior cerebral artery, a superior cerebellar artery, a basilar artery, a left internal acoustic (labyrinthine) artery, an anterior inferior cerebellar artery, a left ascending pharyngeal artery, a posterior inferior cerebellar artery, a deep cervical artery, a highest intercostal artery, a costocervical trunk, a subclavian artery, a middle cerebral artery, an anterior cerebral artery, an anterior communicating artery, an ophthalmic artery, a posterior communicating artery, a facial artery, a lingual artery, a superior laryngeal artery, a superior thyroid artery, an ascending cervical artery, an inferior thyroid artery, a thyrocervical trunk, an internal thoracic artery, and/or any branches thereof The suprathoracic vessels can also comprise at least one of a medial orbitofrontal artery, a recurrent artery (of Heubner), medial and lateral lenticulostriate arteries, a lateral orbitofrontal artery, an ascending frontal (candelabra) artery, an anterior choroidal artery, pontine arteries, an internal acoustic (labyrinthine) artery, an anterior spinal artery, a posterior spinal artery, a posterior medial choroidal artery, a posterior lateral choroidal artery, and/or branches thereof. The suprathoracic vessels can also comprise at least one of perforating arteries, a hypothalamic artery, lenticulostriate arteries, a superior hypophyseal artery, an inferior hypophyseal artery, an anterior thalamostriate artery, a posterior thalamostriate artery, and/or branches thereof. The suprathoracic vessels can also comprise at least one of a precentral (pre-Rolandic) and central (Rolandic) arteries, anterior and posterior parietal arteries, an angular artery, temporal arteries (anterior, middle and posterior), a paracentral artery, a pericallosal artery, a callosomarginal artery, a frontopolar artery, a precuneal artery, a parietooccipital artery, a calcarine artery, an inferior vermian artery, and/or branches thereof.

In some aspects, the suprathoracic vessels can also comprise at least one of diploic veins, an emissary vein, a cerebral vein, a middle meningeal vein, superficial temporal veins, a frontal diploic vein, an anterior temporal diploic vein, a parietal emissary vein, a posterior temporal diploic vein, an occipital emissary vein, an occipital diploic vein, a mastoid emissary vein, a superior cerebral vein, efferent hypophyseal veins, infundibulum (pituitary stalk) and long hypophyseal portal veins, and/or branches thereof.

The intrathoracic vessels can comprise the aorta or branches thereof. For example, the intrathoracic vessels can comprise at least one of an ascending aorta, a descending aorta, an arch of the aorta, and/or branches thereof. The descending aorta can comprise at least one of a thoracic aorta, an abdominal aorta, and/or any branches thereof. The intrathoracic vessels can also comprise at least one of a subclavian artery, an internal thoracic artery, a pericardiacophrenic artery, a right pulmonary artery, a right coronary artery, a brachiocephalic trunk, a pulmonary trunk, a left pulmonary artery, an anterior interventricular artery, and/or branches thereof. The intrathoracic vessels can also comprise at least one of an inferior thyroid artery, a thyrocervical trunk, a vertebral artery, a right bronchial artery, a superior left bronchial artery, an inferior left bronchial artery, aortic esophageal arteries, and/or branches thereof.

In some aspects, the intrathoracic vessels can also comprise at least one of a right internal jugular vein, a right brachiocephalic vein, a subclavian vein, an internal thoracic vein, a pericardiacophrenic vein, a superior vena cava, a right superior pulmonary vein, a left brachiocephalic vein, a left internal jugular vein, a left superior pulmonary vein, an inferior thyroid vein, an external jugular vein, a vertebral vein, a right highest intercostal vein, a 6th right intercostal vein, an azygos vein, an inferior vena cava, a left highest intercostal vein, an accessory hemiazygos vein, a hemiazygos vein, and/or branches thereof.

In some aspects, the subthoracic vessels can comprise at least one of renal arteries, inferior phrenic arteries, a celiac trunk with common hepatic, left gastric and splenic arteries, superior suprarenal arteries, a middle suprarenal artery, an inferior suprarenal artery, a right renal artery, a subcostal artery, 1st to 4th right lumbar arteries, common iliac arteries, an iliolumbar artery, an internal iliac artery, lateral sacral arteries, an external iliac artery, a testicular (ovarian) artery, an ascending branch of deep circumflex iliac artery, a superficial circumflex iliac artery, an inferior epigastric artery, a superficial epigastric artery, a femoral artery, a ductus deferens and testicular artery, a superficial external pudendal artery, a deep external pudendal artery, and/or branches thereof. The subthoracic vessels can also comprise at least one of a superior mesenteric artery, a left renal artery, an abdominal aorta, an inferior mesenteric artery, colic arteries, sigmoid arteries, a superior rectal artery, 5th lumbar arteries, a middle sacral artery, a superior gluteal artery, umbilical and superior vesical arteries, an obturator artery, an inferior vesical and artery to ductus deferens, a middle rectal artery, an internal pudendal artery, an inferior gluteal artery, a cremasteric, pubic (obturator anastomotic) branches of inferior epigastric artery, a left colic artery, rectal arteries, and/or branches thereof.

In some aspects, the lateral thoracic vessels can comprise at least one of humeral arteries, a transverse cervical artery, a suprascapular artery, a dorsal scapular artery, and/or branches thereof. The lateral thoracic vessels can also comprise at least one of an anterior circumflex humeral artery, a posterior circumflex humeral artery, a subscapular artery, a circumflex scapular artery, a brachial artery, a thoracodorsal artery, a lateral thoracic artery, an inferior thyroid artery, a thyrocervical trunk, a subclavian artery, a superior thoracic artery, a thoracoacromial artery, and/or branches thereof.

In some embodiments, a catheter, such as that described in U.S. patent application Ser. No. 12/731,110, which was filed on Mar. 24, 2010, and which is incorporated herein by reference in its entirety, can be used to deliver a stent delivery system. The delivery system can include an expandable occluding device (e.g., stent) configured to be placed across an aneurysm that is delivered through the distal portion of the catheter, out a distal tip, and into the vasculature adjacent an aneurysm in, for example, the middle cerebral artery. A proximal portion of the catheter can remain partially or entirely within a guiding catheter during delivery, and an intermediate portion, taper portion, and distal portion of the catheter can extend distally of the guiding catheter. The occluding device can be released at the target location and can be used to occlude blood flow into the aneurysm. The catheter can be used to reach target locations (e.g., aneurysms) located elsewhere in the body as well, include but not limited to other arteries, branches, and blood vessels such as those described above.

In some embodiments, a method of implantation and monitoring can be used, for example, with the deployment systems described above. The method can include implanting an occluding device within the vasculature of a patient such that the device extends, within and along a vessel, past an aneurysm.

The apparatus and methods discussed herein are not limited to the deployment and use of an occluding device, such as an occluding spiral, or stent within the vascular system but can include any number of further treatment devices and applications. Other treatment sites can include areas or regions of the body such as organ bodies. Modification of each of the above-described apparatus and methods for carrying out the subject technology, and variations of aspects of the disclosure that are apparent to those of skill in the art are intended to be within the scope of the claims. Furthermore, no element, component, or method step is intended to be dedicated to the public regardless of whether the element, component, or method step is explicitly recited in the claims.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations which will be apparent to those skilled in the art can be made in the arrangement, operation and details of the method and apparatus of the subject technology disclosed herein without departing from the spirit and scope of the subject technology as defined in the appended claims. Therefore, the scope of the subject technology should be determined by the appended claims and their legal equivalents. Furthermore, no element, component or method step is intended to be dedicated to the public regardless of whether the element, component or method step is explicitly recited in the claims. Underlined and/or italicized headings and subheadings are used for convenience only, do not limit the subject technology, and are not referred to in connection with the interpretation of the description of the subject technology. In the claims and description, unless otherwise expressed, reference to an element in the singular is not intended to mean "one and only one" unless explicitly stated, but rather is meant to mean "one or more." In addition, it is not necessary for a device or method to address every problem that is solvable by different embodiments of the disclosure in order to be encompassed by the claims.

What is claimed is:

1. A delivery system for implanting a medical device, the system comprising:
 a delivery member configured for insertion into a patient;
 a medical device configured to be severed entirely by electrolysis from the delivery member for placement in the patient; and
 an electrolytically detachable component interconnecting the medical device and the delivery member, the detachable component having at least one electrolytically corrodible first portion being adapted to serve as an anode in electrolytic corrosion when in contact with a body fluid such that the medical device may be severed from the delivery member by electrolysis, the at least one first portion defining a body having an outer surface and at least one surface structure that, when viewed in cross-section along a longitudinal axis of the body, extends inwardly from the outer surface into the body in a zig-zag serrated pattern such that the body has a cross-sectional profile that includes at least one peak and at least one valley.

2. The system of claim 1, wherein the at least one surface structure extends in a longitudinal direction of the detachable component.

3. The system of claim 1, wherein the at least one surface structure comprises a groove extending in a longitudinal direction of the detachable component.

4. The system of claim 1, wherein the at least one surface structure comprises a plurality of surface structures.

5. The system of claim 4, wherein the plurality of surface structures collectively form a rough surface on the first portion.

6. The system of claim 1, wherein the first portion defines a starburst shaped cross section.

7. The system of claim 1, wherein the first portion defines an oblong cross section having a perimeter formed with a plurality of peaks and valleys.

8. The system of claim 1, wherein the first portion comprises an upper surface having a plurality of peaks and valleys formed thereon.

9. The system of claim 8, wherein the first portion further comprises a lower surface having a plurality of peaks and valleys formed thereon.

10. The system of claim 1, wherein the detachable component is designed to be continuously electrically conductive in the proximal-to-distal direction.

11. The system of claim 1, wherein the detachable component further comprises at least one non-corrodible second portion adjacent to the first portion.

12. The system of claim 1, further comprising a source of electrical power, a cathode, and a catheter, wherein the detachable component, the medical device, and the delivery member are configured to slide within the catheter.

13. The system of claim 1, wherein the at least one peak comprises a plurality of peaks, and the least one valley comprises a plurality of valleys, wherein on a side of the first portion each of the plurality of peaks and valleys are spaced apart from an adjacent peak or valley at a common distance.

14. The system of claim 1, wherein the at least one valley comprises a plurality of valleys, each of the plurality of valleys having a common width.

15. The system of claim 1, wherein the first portion comprises a ribbon-shaped cross-sectional profile.

16. An electrolytically detachable component for interconnecting a medical device with a delivery member, the component adapted to serve as an anode to be severed entirely by electrolysis in body cavities or blood vessels, the component comprising:
   a first portion attached to the medical device and the delivery member, the first portion being electrolytically corrodible, the first portion defining a continuous, elongate body having at least one surface structure formed therein that, when viewed in cross-section along a longitudinal axis of the body, defines recesses providing surface area on the first portion in a zig-zag serrated pattern for enhancing electrolytic corrosion of the first portion when in contact with a body fluid.

17. The component of claim 16, wherein the at least one surface structure comprises an elongate trough extending in a longitudinal direction along the elongate body of the first portion.

18. The component of claim 16, wherein the elongate body of the first portion defines an oblong cross section.

19. The component of claim 16, wherein the elongate body of the first portion defines a starburst shaped cross section.

20. The component of claim 16, wherein the elongate body of the first portion defines a cross section formed from at least one concavity and at least one convexity.

21. The component of claim 20, wherein the at least one concavity is formed by a pair of substantially linear edges.

22. The component of claim 16, wherein the first portion comprises additional recesses, the recess and the additional recesses forming a plurality of peaks and valleys, wherein on a side of the first portion each of the plurality of peaks and valleys are spaced apart from an adjacent valley or peak at a common distance.

23. The component of claim 16, wherein the first portion comprises additional recesses, the recess and the additional recesses forming a plurality of peaks and valleys, each of the plurality of valleys having a common width.

24. The component of claim 16, wherein the first portion comprises a ribbon-shaped cross-sectional profile.

* * * * *